US010191009B2

United States Patent
Marei et al.

(10) Patent No.: US 10,191,009 B2
(45) Date of Patent: Jan. 29, 2019

(54) ELECTROCHEMICAL DETERMINATION OF HEAVY METALS

(71) Applicant: University of Louisville Research Foundation, Inc., Louisville, KY (US)

(72) Inventors: Mohamed M. Marei, Louisville, KY (US); Richard P. Baldwin, Louisville, KY (US); Thomas J. Roussel, Jr., Louisville, KY (US); Robert S. Keynton, Louisville, KY (US)

(73) Assignee: UNIVERSITY OF LOUISVILLE RESEARCH FOUNDATION, INC., Louisville, KY (US)

( * ) Notice: Subject to any disclaimer, the term of this patent is extended or adjusted under 35 U.S.C. 154(b) by 413 days.

(21) Appl. No.: 15/061,194

(22) Filed: Mar. 4, 2016

(65) Prior Publication Data

US 2016/0258900 A1 Sep. 8, 2016

Related U.S. Application Data

(60) Provisional application No. 62/128,953, filed on Mar. 5, 2015.

(51) Int. Cl.
G01N 27/42 (2006.01)

(52) U.S. Cl.
CPC .................... G01N 27/423 (2013.01)

(58) Field of Classification Search
CPC .................................................... G01N 27/423
See application file for complete search history.

(56) References Cited

U.S. PATENT DOCUMENTS

| 2010/0224489 A1* | 9/2010 | Chapman | G01N 27/4161 204/412 |
| 2010/0252450 A1* | 10/2010 | Riehl | B82Y 15/00 205/775 |
| 2016/0231269 A1* | 8/2016 | Kumar Ghosh | C23C 14/205 |

OTHER PUBLICATIONS

Marei et al. (M.M. Marei, T.J. Roussel, R.S. Keynton, R.P. Baldwin, Electrochemical and microfabrication strategies for remotely operated smart chemical sensors: Application of anodic stripping coulometry to calibration-free measurements of copper and mercury, Analytica Chimica Acta 803 (2013) 47-55) (Year: 2013).*

Bonfil et al. (Y. Bonfil, E. Kirowa-Eisner, Determination of nanomolar concentrations of lead and cadmium by anodic-stripping voltammetry at the silver electrode, Analytica Chimica Acta 457 (2002) 285-296) (Year: 2002).*

(Continued)

*Primary Examiner* — Gurpreet Kaur
*Assistant Examiner* — Joshua L Allen
(74) *Attorney, Agent, or Firm* — Wyatt, Tarrant & Combs, LLP; Stephen C. Hall

(57) ABSTRACT

Methods and sensing instruments are provided which perform automated electrochemical sensing and determination of metals in a liquid sample, such as drinking water or waste water. With use of microelectrode arrays, concentrations of metal are determined through a double potential step variation on anodic stripping coulometry, and the ability to generate these results provides for compact sensor networks that can be remotely deployed for determination of metals in samples, for real-time, decentralized sample monitoring.

8 Claims, 8 Drawing Sheets

(56) References Cited

OTHER PUBLICATIONS

Hoyer et al. (B Hoyer, L Kryger, Application of the generalized standard addition method to correction for the effects of peak overlap and intermetallic compound formation in potentiometric stripping analysis, Analytica Chemica Acta 167 (1985) 11-21). (Year: 1985).*

Lazar et al. (B Lazar, S Ben-Yaakov, Subtractive differential pulse anodic stripping voltammetry at a stationary mercury-coated glassy carbon electrode 108 (1980) 143-115). (Year: 1980).*

Sipos et al. (L Sipos, S Kozar, I Kontusic, M Branica, Subtractive anodic stripping voltammetry with rotating mercury coated glassy carbon electrode 87 (1978) 347-352). (Year: 1978).*

Marei, M.M.; Roussel, T.J.; Keynton, R.S.; Baldwin, R.P.; Electrochemical Determination of As(III) by Subtractive Anodic Stripping Coulometry in a Microfabricated Platform; Presentation, Mar. 5, 2014; pp. 1-49; PITTCON Conference & Expo, Chicago, IL, U.S.

Eggli, R.; Anodic Stripping Coulometry at a Thin-Film Mercury Electrode. Anal. Chim. Acta; 1977; vol. 91; pp. 129-138; U.S.

Marei, M.M.; Roussel, T.J.; Keynton, R.S.; Baldwin, R.P.; Electrochemical and microfabrication strategies for remotely operated smart chemical sensors: Application of anodic stripping coulometry to calibration-free measurements of copper and mercury. Anal. Chim. Acta 2013, vol. 803, pp. 47-55; U.S.

Economou, A.; Recent Developments in on-line electrochemical stripping analysis—An overview of the last 12 years.; Anal. Chim. Acta; 2010; vol. 683; pp. 38-51; U.S.

Bonfil, Y.; Brand, M.; Kirowa-Eisner, E.; Characteristics of subtractive anodic stripping voltammetry of lead, cadmium and thallium at silver-gold alloy electrodes.; Electroanalysis; 2003; vol. 15; pp. 1369-1376; U.S.

Marei, M.M.; Roussel, T.J.; Keynton, R.S.; Baldwin, R.P.; Calibration-free Micro-fabricated Electrochemical Sensor for Heavy Metal Determination, Mar. 2013; pp. 1-25; PITTCON Conference & Expo, Philadelphia, PA., U.S.

Marei, M.M., "Electrochemical and microfabrication strategies for remotely operated heavy metal sensor networks for water analysis : the dual challenges of calibration-less measurement and sample pretreatment," Aug. 2014, pp. 1-191, Electronic Theses and Dissertations, Paper 905. Retrieved from: http://dx.doi.org/10.18297/etd/905.

Marei, M.M., Baldwin, R.P, Keynton, R.S., Roussel, T.J., "Electrochemical Determination of As(III) by Substractive Anodic Stripping Coulemetry in a Micro-Fabricated Platform," Conference Abstract, In: PITTCON Conference & Expo 2014, Mar. 2-6, 2014, total pp. 1-1860; Chicago, IL; Technical Program, Agenda of Sessions, p. 1420, Session No. 1900, Abstract No. 1900-3.

* cited by examiner

A – Macro electrode

B - - Microelectrode array

ELECTROCHEMICAL DETERMINATION OF HEAVY METALS

CROSS REFERENCE TO RELATED U.S. APPLICATION

This application claims the benefit of priority to U.S. Provisional Application No. 62/128,953, which was filed on Mar. 5, 2015, the contents of which are incorporated herein by reference.

FIELD OF INVENTION

Embodiments described herein relate to methods and sensing instruments for measuring levels of one or more analytes of interest—such as metals—from samples of water or other liquid samples, including for samples that are likely to contain interferents having the potential to affect coulometric signals associated the primary analyte of interest.

BACKGROUND

Much of the drinking water in this country, as well as water for irrigation or other uses, comes from—or comes in contact with—natural waters that include rivers, streams, and ground water. Various metals are among the types of contaminants found in natural waters. Monitoring for the presence of metals—such as arsenic, copper, cadmium, mercury, and lead, among others—is desirable and essential. Although monitoring is possible, conventional monitoring techniques are not well automated, or scalable. Rather, these require manual steps which are not only labor- and time-intensive, but also expensive to carry out.

Conversely, labor, time, and cost can be reduced in proportion to the ability to monitor water quality in a manner that is substantially automated. A desirable level of automation would involve keeping the monitoring steps independent of continuous operator intervention, and without the need for manual calibration.

There have been prior techniques for monitoring water quality and analyzing for contaminants. Some have employed electrochemical approaches that involve the detection and analysis of signals associated with a metal-containing sample in the presence of an electrolyte and an electrode or an electrode array, such as when a metal is deposited on an electrode or stripped from an electrode under a known potential. Because stripping is the reverse of the deposition process, absolute charge for deposition process ($Q_{dep}$) generally equals that of stripping ($Q_{strip}$). Such techniques can be configured to detect the presence of metals, and to characterize them based on differences in signals associated with the electrical current needed to cause deposition or stripping, as the case may be depending on how the test is set up. One example of this is seen in efforts that have focused on stripping analysis, which is one of the more sensitive of the electrochemical analytical techniques for metals. Problematically, at least from a perspective of scalability, many prior stripping methods for metal determination require a high level of operator intervention and experience, largely owing to the variable nature of the electrode surface/electrolyte interface and the necessity for having an operator perform blank subtraction and calibration.

Consequently, prior systems and techniques have not been able to achieve the needed level of automation, or scalability, because the signals depend on multiple variables that change over time or even over the course of a day. These variables include the temperature and humidity of the testing environment, the viscosity of the sample, and other factors that can affect mass transport rates of metals and metal-containing particles in a sample. Consequently, the accuracy of prior approaches depends on regular calibration of the sensors and analytical instrumentation.

Moreover, in the natural state, the metal(s) of interest are typically dissolved in the water or other liquid sample being tested. Not only does the metal(s) dissolved in this solvent produce a signal in response to electrochemical events, but the solvents also produce background signals that must be corrected for. Consequently, prior approaches have included the use of separate, blank electrolytes from which metals have been purged. Although such approaches allow for background correction, this again increases labor, time, and costs associated with monitoring of samples. An operator must be present on site who will run the analytical test on the blank, then run the test again on the sample, so that the signal(s) attributable to analyte(s) of interest can be determined. Because the environment within or leading to the analytical instrument might vary widely in terms of temperature, humidity, pH, viscosity, and other variables, the need for calibration will be frequent, and time-consuming.

Further, not only does the testing environment affect the uniformity of results, but the condition of the working electrode changes over time, as well. Fouling of the working electrode through natural deposits and particulates such as silt and organic matter result in passivation of the electrode surface, increases the time required for analytes of interest to diffuse to the electrode surface, and diminishes the quality, consistency, or both of the signal required to make the necessary determinations.

Unfortunately, the likelihood for inaccuracies and inconsistent performance over time, which previously was associated with automated monitoring for metals and other contaminants in water, has prompted a decrease in the level of automation, with a corresponding increase in human operator involvement in the testing process. This, inevitably, results in less frequent testing and fewer testing centers. It also means that delays are inherent in that sampling and testing occur in separate places, and at different times—often hours or days apart. Conversely, there is a significant and long-felt need to increase testing frequency and regularity, and to facilitate decentralized testing at remote locations, in a manner that requires less operator involvement. Likewise, the need exists for accurate detection and determination of metals in water and other liquid samples that may contain dissolved metals in them. Additionally, the need exists to reduce operator involvement and increase automation, storing testing data that can be communicated from a remote location in real time. Preferably, these capabilities are to occur in a time frame conducive to high throughput (e.g., 1-2 minutes or less) while being performed remotely, and without operator involvement and without need for ongoing manual calibration. The need exists not only to analyze for a single metal ion, but to test actual real-world samples and distinguish between various metal atoms or species that might be found in them. In short, there is a widely recognized need for automated, compact, remotely deployed sensor networks for determination of metal content (both detection and quantification) in liquid samples.

One advantage of the present embodiments rests in the fact that, unlike other electrochemical analytical methods, the acquired signals—which are obtained by exhaustive coulometry as explained further—are not substantially dependent on variables that affect mass transport rates within the testing medium. Furthermore, the signals acquired by practicing present embodiments are not as significantly vulnerable to changes to the working electrode surface that necessarily occur over time, such as fouling. This reduces the need to change the sensors as frequently as would otherwise be the case. Another advantage is the time-, labor-, and costs—savings by the automated nature and the reduction in time between sample collection and analysis. All of these objects, and additional ones, are met based on the disclosures contained herein as claimed according to these multiple embodiments, and their alternatives.

SUMMARY OF EMBODIMENTS

A chemical analysis system capable of remote deployment according to multiple embodiments and alternatives utilizes microfabricated sensors, which can be relatively inexpensive to manufacture, for electrochemical sensing and determination of metals in a liquid sample, such as drinking water or waste water prior to or during treatment. In some embodiments, a thin layer, constant volume cell utilizes Faraday's law to calculate the concentration of a metal. Because the systems are meant for remote deployment, embodiments preferably use a low-power, energy-conserving, battery-powered microcontroller, or like components, for storing and executing program code to initiate automated sample loading, to control flow into the sensor, to conduct discrete analyses continuously at predetermined intervals, and to store analytical results, among other steps. In some embodiments, a technique, referred to as double potential step-anodic stripping coulometry (DPS-ASC), is implemented to produce background-corrected linear relationships of the stripping signals for metals without need of a calibration step performed manually. Depending on electrode surface area and the particular analyte, linear relationships are generally found at a wide range of concentrations and provide automated calibration at detection limits down to about 1 ppb (parts per billion).

The current embodiments are useful to detect particular metals as well as particular species of metals. For example, arsenic can exist in a variety of oxidation states, including elemental arsenic—As(0), arsenide—As(3−), arsenite—As (III), and arsenate—As(V). Thus, the inorganic forms, As(III) and As(V), are the most common species in ground and surface waters, and both species are more toxic than organic arsenic forms. As(III), generally, is more prevalent than As(V) in groundwater, where entry most frequently occurs by dissolution of arsenic rich soil deposits. While the species of arsenic, particularly arsenite and arsenate are discussed here in some detail, other analytes are contemplated, including copper, cadmium, mercury, and lead. In short, the embodiments are not limited to any particular analyte. These can be used for detection of metals, including those compounds where the reduced and oxidized species involve one form that dissolves in the electrolyte and another form that is insoluble that accumulates on the electrode surface. The capabilities of present embodiments provide desirable selectivity—performing the analysis at multiple deposition potentials quantitatively resolves the contributions of individual metals from the total stripping signal—and likewise tolerate possible interference by other metals or compounds than the analytes of interest.

Regardless of the analyte, present embodiments capitalize upon electrolysis occurring in a cell of constant and known volume. Faraday's law is expressed as:

$Q=nFVC,$ where Q is the absolute charge required for stripping (in coulombs, or microcoulombs), n is the characteristic number of valence shell electrons (i.e., number of electrons per mole, or oxidation number) for a particular metal or species, F is the Faraday constant expressed in coulombs per mole of charge (i.e., to three significant figures, F is $9.65 \times 10^4$), C is the concentration of a particular metal or species in the solution, and V is the volume of the cell. Accordingly, the absolute charge required for stripping can be determined, the oxidation states of particular metals and species typically found in natural waters are known, and cell volume can be kept constant. As a result, one can quantitatively determine the concentration of a metal according to the equation:

$$C = \frac{Q}{nFV}$$

Obtaining the signals during a period of stripping (oxidation) makes the measurement independent of experimental conditions, such as temperature, humidity, viscosity, as well as other factors that limit surface area on an electrode such as partial fouling. Generally, the method involves applying a constant voltage to exhaustively pre-concentrate all dissolved metals in a sample by reducing free dissolved metal cations to their insoluble metallic forms, which deposit upon an electrode. In some aspects as will be discussed, the method works by exhaustive deposition onto an electrode (which can be referred to, generally, as a macro electrode) or a microelectrode array, followed by oxidative stripping under constant potential and recording of stripping current. An example of a microelectrode array would be similar to the fabrication of a gold electrode as discussed here, with some modification such as a silicon nitride layer deposited and photolithographically patterned over the gold layer. The additional layer reduces the effective surface area of the gold electrode, thereby providing a more favorable signal to noise ratio. Although the specific sequence, number, and length of potential steps may be optimized and adjusted for a given application, various sequences are provided herein. One such approach, again in non-limiting fashion, provides background correction carried out on site (i.e., in the sample solution) by first having a negligible pre-concentration period (i.e., non-exhaustive deposition on the electrode), then recording a stripping charge in the sample solution, then initiating exhaustive deposition followed by stripping, where the analytical signal is derived from comparing only the two potential steps where stripping occurs. The difference between the integrated current signals is obtained and then incorporated within the equation of Faraday's law, and concentration is determined.

Accordingly, systems and methods provided for among the present embodiments are durable, reusable, relatively inexpensive to make and maintain. Numerous sensors can be configured according to these embodiments, which collectively are capable of being connected within a network for real-time, online, remote, decentralized monitoring at many testing sites. Preferably, such systems are optimized to use and conserve battery power to allow for remote analysis and storage/transmission of results. Present embodiments can be used to screen samples and determine when to send for laboratory testing and analysis, thus reducing the overall burden on the testing infrastructure. Moreover, following initial deployment, present embodiments can be accomplished without use of human operators.

The current embodiments provide sensor performance with suitable sensitivity attainable at trace levels for analysis of metals and metal-containing species, without need for calibration. The approaches discussed here reduce the background signals and offer correction by means of a near zero intercept of a linear calibration plot. Further advantages associated with the present embodiments will be evident from the current disclosure.

DESCRIPTION OF FIGURES

The drawings, schematics, figures, and descriptions herein are to be understood as illustrative of steps, structures, features and aspects of the present embodiments and do not limit the scope of the embodiments. The scope of the application is not limited to the precise arrangements or scales as shown in the figures.

MULTIPLE EMBODIMENTS AND ALTERNATIVES

Figure 1:
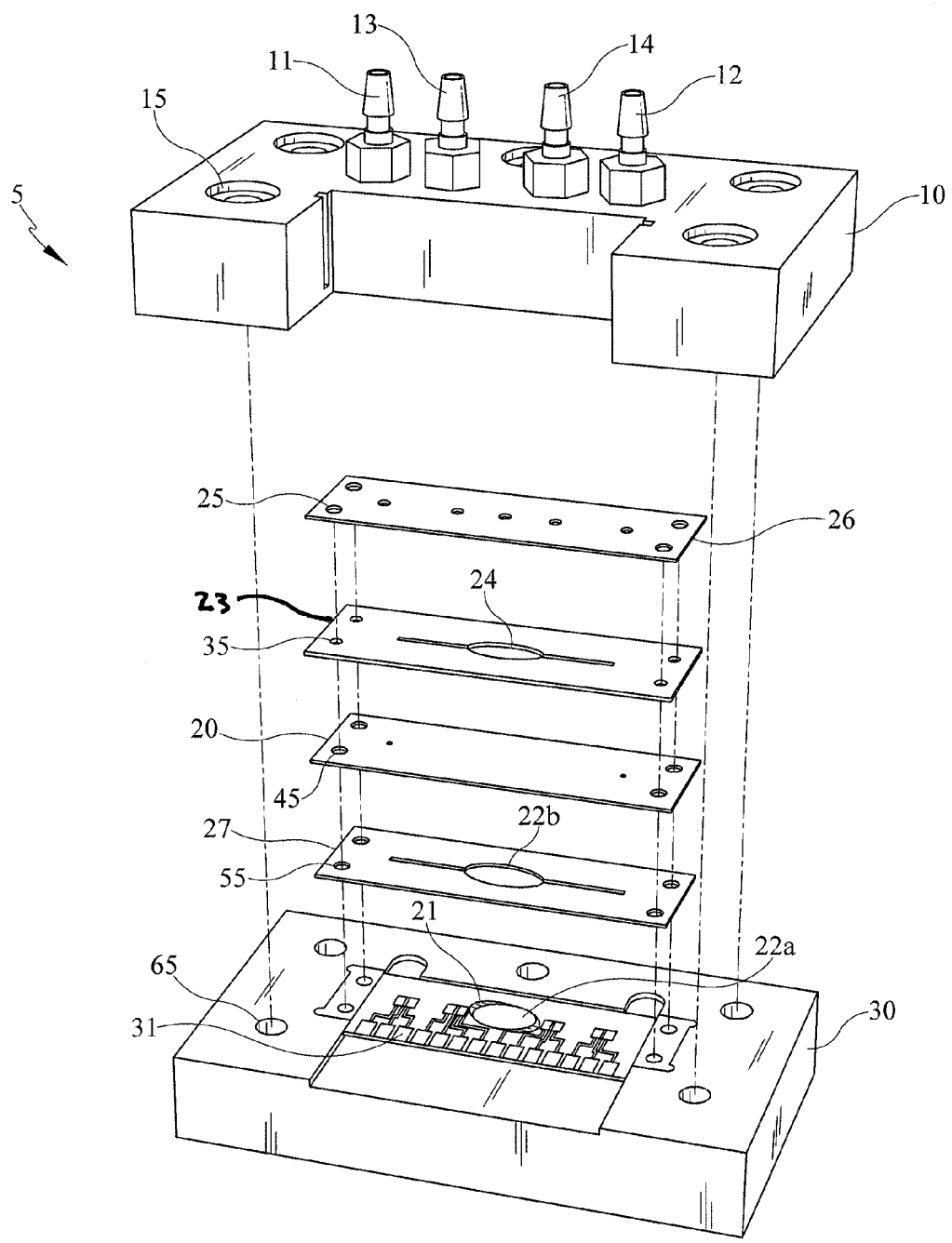
FIG. 1 is an exploded view of an anodic stripping coulometry platform assembly incorporating a thin layer cell, according to multiple embodiments and alternatives.

The invention applies to a wide range of testing environments, with the ability to detect and quantify various metals and metal-containing species, with detections capabilities at or below 1 ppb. In certain embodiments, a flow cell assembly comprises a sensor chip containing a working electrode, a counter electrode, respective compartments a the working electrode and a counter electrode, the former for receiving a sample solution with analytes of interest, and a membrane isolating the respective compartments to limit the exchange of byproducts between them. The components of such an assembly are housed within a structure having upper and lower fixtures. As desired, additional items as known in the art such as rubber sealing gasket layers are used. In general, the electrolyte is an aqueous liquid. In some embodiments, the flow cell assembly yields a three electrode dual compartment cell with independent flow paths communicating with the working electrode and counter electrode, respectively. Embodiments are not limited to those having three electrodes and two compartments. Other kinds of compartment arrangements and electrode configurations are within the scope of these embodiments.

In certain embodiments, a low-power microcontroller, for example, is connected to a custom potentiostat, programmable for use in micro-power electrochemical-sensing applications. The microcontroller controls automated sample loading capabilities that use DC-powered micropumps/microvalves connected in-line with the sample inlet. In some embodiments the sample moves at a flow rate of about of 1 µL-100 µL/min. Additionally, in some embodiments, the microcontroller is configured to perform analyses periodically (e.g., 10-20 times per day), write data to local storage (e.g., microSD memory card) for later retrieval, and switch into sleep mode between measurements to save power. Various alternative forms of memory as known in the art can be used for storage. Optionally, an inexpensive solar panel as known in the art is used to constantly charge a 7.2V (2200 mAh) lithium-ion battery which powers the system (approximately ~35 mA current draw during a 60 sec experiment). In short, because the electronics consume minimal power during operation, while being powered by one or more solar-replenished batteries, the automated analytical system will operate remotely for long durations and without operator intervention. As desired, signal enhancement during the stripping phases is achieved by amplification and other techniques known in the art. It will be appreciated that other components that provide programmable logic are suitable for the functions provided by the microcontroller. A complex programmable logic device (CPLD) and a field programmable gate array (FPGA) are two examples, but there are others known to those having skill in the art.

A gold electrode on a silicon dioxide coated wafer is one example of a suitable working electrode contained within the cell. In an example fabrication, the gold electrode is patterned atop a nickel adhesion layer on the wafer using an image reversal photolithographic liftoff technique as known in the art. Buffered oxide etching is used to form recesses into which the electrode material is added by successive sputtering steps to form the patterned wafer. As well, other known techniques also exist and will be readily recognized for forming a microelectrode array suitable for practicing with the current embodiments.

FIG. 1 provides an exploded view illustrating a platform assembly 5 containing a thin layer cell of a type that can be utilized for double potential step-anodic stripping coulometry (DPS-ADS) according to present embodiments. Upper and lower fixtures 10 and 30 connect and provide a housing for an anodic stripping coulometry platform. Appropriate materials for these fixtures include polycarbonate, ceramic, silicone, and other non-conductive, inert materials. Sample inlet 11 opens to a flow path wherein sample flows to, and through, a working electrode compartment 22 in order to make contact with working electrode 21. In FIG. 1, the working electrode compartment is layered and shown as 22a and 22b, with 22b optionally being formed as a cavity in layer 27. In some embodiments, working electrode 21 is incorporated with sensor chip 31 or other integrated circuitry providing additional functions as described herein. The flow path further communicates to outlet 12 to allow removal of a sample. Flow into and throughout the cell may be controlled by micropumps and valves (not shown) which can be set up according to methods known in the art. As desired, additional openings, channels, or grooves may be provided for accommodating flow within compartments.

Still referring to FIG. 1, counter electrode 26 is positioned at one wall of counter electrode compartment 24. A pyrolytic graphite sheet is suitable for counter electrode 26. Membrane 20 isolates compartments 22, 24. Another inlet/outlet combination, 13, 14 respectively, is used for adding and removing electrolyte to the counter electrode compartment 24. As desired, sealing layers 23, 27 (i.e., rubber gaskets) are used for sealing the respective compartments, and additional gasket layers may be implemented as well. Such a platform assembly 5 for the thin layer cell is secured by alignment pins (not shown, but broken lines indicate how the cell is pulled together) inserted through top and bottom fixtures. Several holes for accommodating or receiving alignment pins are shown in FIG. 1. As desired, threaded pins with compatible threading in the holes are used. For brevity, not all the holes are labeled. Holes 15 and 65 are labeled, and are representative of holes formed in the top and bottom fixtures for threaded screws (not shown) that tighten the assembly. Likewise, several through-holes for the pins to pass through are formed in interior levels within the cell. For illustration, FIG. 1 labels several of the through-holes, including through-hole 25 (formed in electrode layer 26), through-hole 35 (formed in sealing layer 23 associated with the counter electrode compartment), through-hole 45 (formed in membrane 20), and through-hole 55 (formed in sealing layer 27). Through-holes can be cut or otherwise formed in these interior layers at fabrication through methods known in the art.

Figure 2:
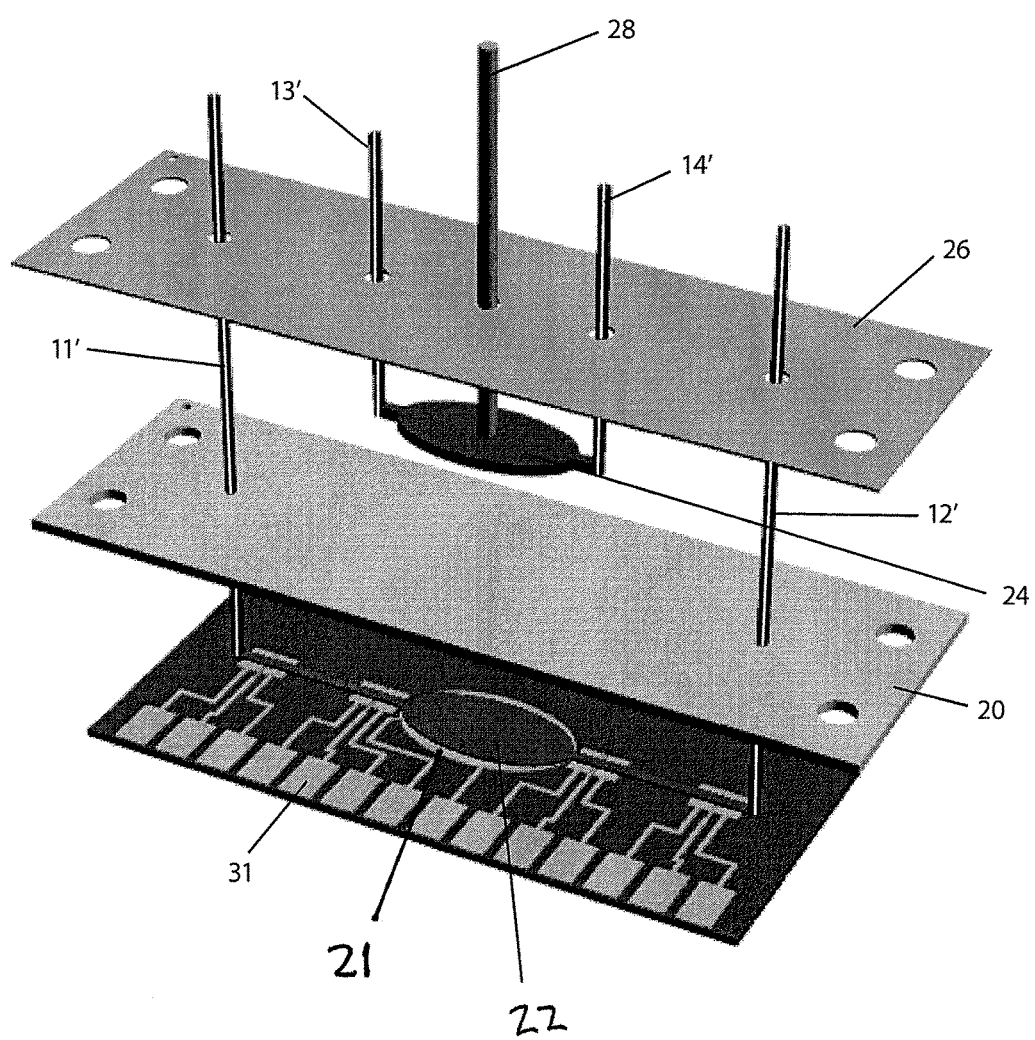
FIG. 2 shows a schematic representation of an anodic stripping coulometry platform incorporating a thin layer cell, according to multiple embodiments and alternatives.

FIG. 2 is a schematic representation of an anodic stripping coulometry platform (with some of the aforementioned structural layers omitted for clarity). Here, reference electrode 28 is provided in communication with the counter electrode compartment 24. In some embodiments, reference electrode 28 is a cylindrical 0.8 mm diameter Ag/AgCl electrode, and counter electrode 26 is a pyrolytic graphite sheet compatible with counter electrode compartment 24, which may have dimensions of about 4 mm×8 mm×0.5 mm. At least a portion of a working electrode compartment 22 may be formed in a layer having dimensions of about 4 mm×8 mm×75 µm. In some embodiments, working electrode 21 is a lithographically patterned 5 mm×8 mm elliptical electrode. This type of example provides, in non-limiting fashion, a three-electrode, dual compartment cell with independent stop-valve controlled flow paths for the working electrode compartment 22 and the counter electrode compartment 24. Flow paths for sample associated with a working electrode compartment are depicted along path 11' (to coincide as though originating from inlet 11 of FIG. 1) and along path 12' (to coincide as though terminating at outlet 12 of FIG. 1), passing over working electrode 21 therebetween. Likewise, flow paths are depicted, in connection with counter electrode compartment 24, along path 13' (to coincide as though originating from inlet 13 of FIG. 1) and along path 14' (to coincide as though terminating at outlet 14 of FIG. 1), communicating with electrode 26. These paths, namely 11' to 12' and 13' to 14', respectively, are isolated by membrane 20 as shown in the schematic.

Figure 3A:
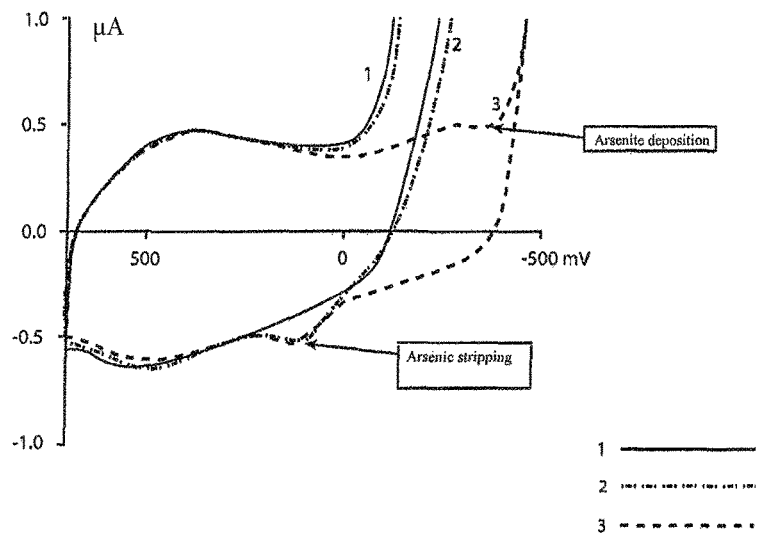
FIG. 3A is a portion of a cyclic voltammogram that provides graphical results of potential steps involving arsenite in a 10 mM HNO3/10 mM NaCl electrolyte, which offers an expanded view over the range +/−1 µA of the cyclic voltammogram of FIG. 3B.
Figure 3B:
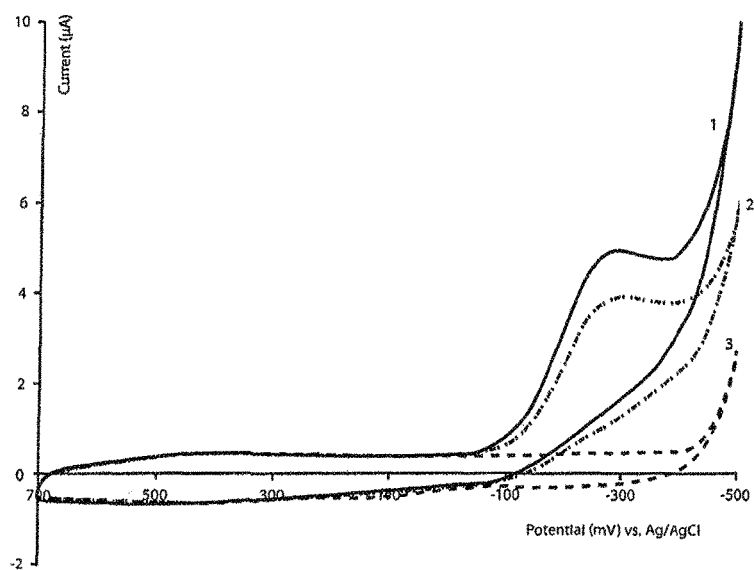
FIG. 3B is a complete cyclic voltammogram from which FIG. 3A was obtained.

Using arsenite-containing samples as an example, arsenite deposition and stripping processes were conducted and investigated by cyclic voltammetry (CV), in the presence of an electrolyte of known pH (~2). Such processes are described in Feeney, R.; Kounaves, S. P, "On-site analysis of arsenic in groundwater using a microfabricated gold ultra-microelectrode array," Anal. Chem. 2000, 72, 2222-28. Because metallic arsenic is a semiconductor and does not readily electrodeposit on itself, relatively low arsenite concentrations were used, providing sub-monolayer coverage on the electrode surface at deposition. Curve 1 of FIGS. 3A and 3B represents the electrolyte-only voltammetry, with a reduction peak for dissolved oxygen beginning at 0 mV (millivolts). Curve 2 represents the electrolyte plus 2.5 µM arsenite (187 ppb), where the arsenite deposition peak is not readily distinguished from the oxygen reduction peak. Notably, the difference between these two traces is the small arsenic stripping peak at +100 mV as seen well in FIG. 3A.

In turn, curve 3 represents further investigation of the arsenite stripping response to rule out the occurrence of interference by the oxygen reduction reaction, or its byproducts. Purging with nitrogen to remove oxygen from the arsenite-containing sample (represented by curve 3) enables clear visualization of the arsenite deposition peak, which is well seen in FIG. 3A at approximately −300 mV. The magnitude of this peak is comparable to the arsenic stripping peak of curve 2, indicating that these peaks represent the Arsenite/Arsenic redox couple. In this example, there was no significant effect on the arsenic stripping peak by the reduction of dissolved oxygen. In some embodiments, a separate system for removing dissolved oxygen or other dissolved gases can be employed upstream of the deposition and stripping processes involving the sample. An example of such a system and method is found in the published patent application, United States Publication No. 20150343372, "Pre-Treatment of Samples by Electrochemical Removal of Dissolved Gases." The contents of this application are fully incorporated herein by reference.

FIG. 3B stands for the proposition that potentials of −500 mV and 500 mV are suitable for arsenite/arsenic deposition and stripping processes, respectively. Consequently, the same potentials were used in analyzing arsenite through double potential step anodic stripping coulometry (DPS-ASC). As a point of comparison, conventional arsenite determination using anodic stripping coulometry can be carried out by (1) stepping the applied potential to −500 mV, (2) recording the reduction current for 60 seconds until all the arsenite in the cell has been exhaustively deposited onto the working electrode, and (3) integrating the resulting amperogram over time to obtain the corresponding charge. The drawback, however, is that deposition involves mass transfer and is, therefore, diffusion-limited and prone to other practical hurdles in the field, such as fouling and the need to monitor current related to oxygen reduction. Consequently, the integral of the deposition signal contains an unfavorable signal-to-noise ratio, and detection levels can only be reached at higher concentrations.

By contrast, utilizing the stripping step and recording the current and charge data during stripping provides several advantages. For example, stripping proceeds much faster than deposition (e.g., 100-200 msec compared to 60 seconds for deposition) so it is not prone to diffusion limitations, nor is stripping dependent on mass transfer. Consequently, the integral of the stripping signal contains considerably less noise, and detection levels are extended down to much lower concentrations.

Figure 4A:
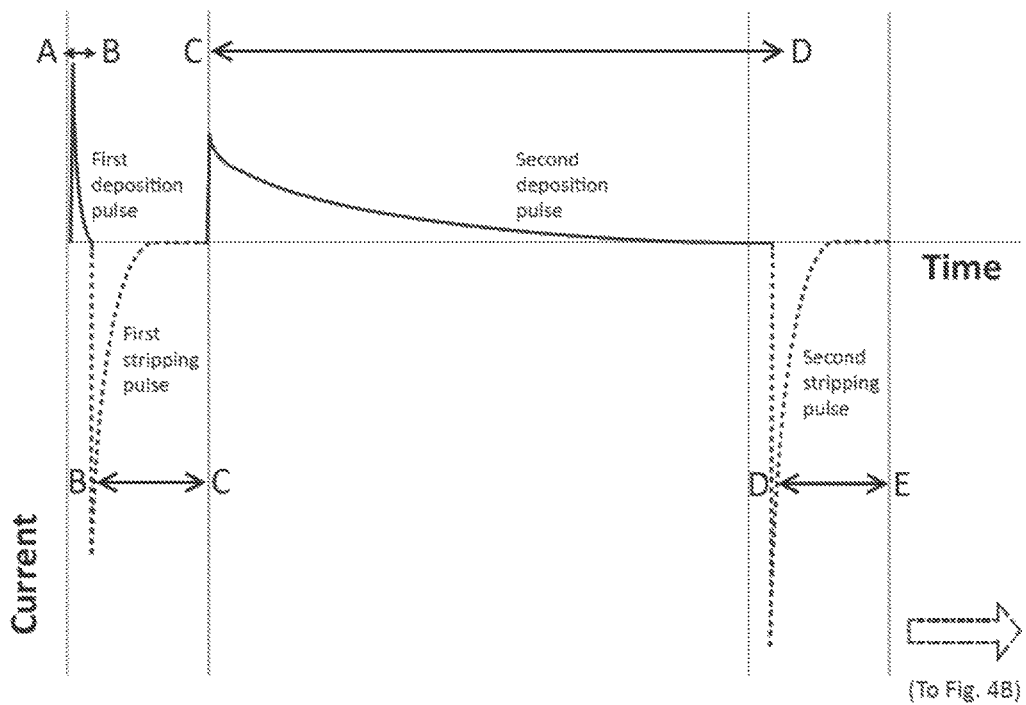
FIGS. 4A-4B illustrate recorded currents during double potential step Anodic stripping (DPS-ASC) pulse sequences, which were performed on a suitable anodic stripping coulometry platform incorporating a thin layer cell, according to multiple embodiments and alternatives.
Figure 4B:
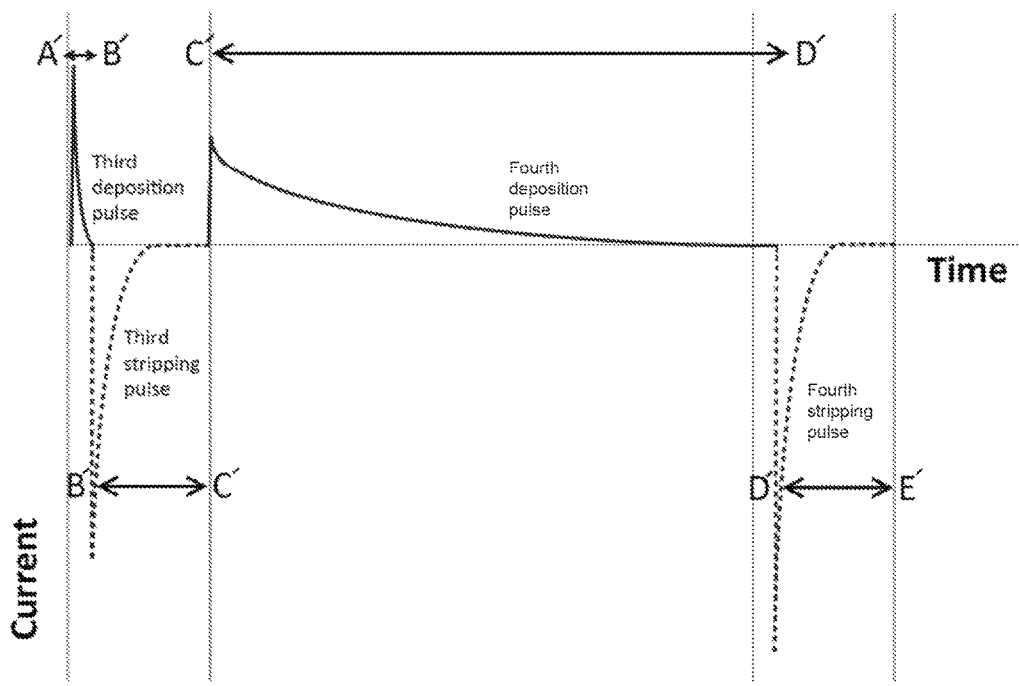

Additionally, present embodiments enable background correction in the sample solution itself through double potential steps. On FIGS. 4A-4B, the horizontal is time intervals over which a sequence of potential steps occurred. Solid lines relate to deposition through reduction. Broken lines relate to oxidative stripping steps. As FIG. 4A shows in the form of a sequence of applied potentials, a negligible pre-concentration period occurs at negative potential (represented at points A to B on the curve, and referred to as "First deposition pulse"). In some embodiments, the pre-concentration is kept short to reduce the percentage of metal content in the sample solution that deposits on the electrode, which helps to improve the signal to noise ratio in later steps. This pre-concentration is followed by a first stripping pulse (B to C), for example at 500 mV, and the stripping charge is monitored and recorded. The charge associated with this first stripping phase is considered the background charge that later will be subtracted as part of background correction. After the first stripping pulse, one or more of the metal(s) is exhaustively deposited on the working electrode during a second deposition pulse (C to D), while at least one dissolved metal referred to herein as an analyte—is not deposited at this potential. Then, a second stripping pulse (D to E) is applied, and the stripping charge is monitored and recorded here again. Likewise, FIG. 4B shows a continuation of the sequence of applied potentials wherein a third deposition pulse occurs at points A' to B'. This is at a potential (i.e., the second deposition potential) that differs from that of the first deposition potential. Next, a third stripping pulse follows (B' to C'), which is the third oxidation reaction in a sequence. After this third oxidation reaction, a fourth deposition pulse initiates a fourth reduction reaction (C' to D') that results in exhaustive deposition of the one or more dissolved metals deposited at the first deposition potential, and the analyte. Next in sequence is a fourth stripping pulse (D' to E') to strip the just-deposited metals, and this stripping charge is monitored and recorded.

In an embodiment, the pre-concentration deposition (A to B, as shown in FIG. 4) at −500 mV occurs only briefly, for about 100 msec as an example. Then, the first stripping pulse (B to C) to remove the negligible quantity of deposited arsenic occurs, at 500 mV, again over a brief period of time (e.g., 320 msec has been used). But when the deposition potential is next applied (C to D), this happens for a period sufficient to ensure exhaustive deposition of the arsenite on the electrode, e.g., 60 seconds. Because stripping of all metals from the electrode occurs rapidly, and is not dependent on factors such as mass transfer, the second stripping pulse (D to E) need only be the same brief period as the first stripping pulse (e.g., about 320 msec). Here, the analytical signal is derived by comparing only the two potential steps where stripping occurs. That is, one subtracts the integral of the signal of the first stripping pulse from that of the second stripping pulse. Accordingly, the resulting method has been referred to as double potential step anodic stripping coulometry (DPS-ASC).

In view of the above, Table I shows the results of the DPS-ASC method at −500 mV (deposition potential) and 500 mV (stripping potential) for various arsenite concentrations expressed in parts per billion (ppb).

Figure 5:
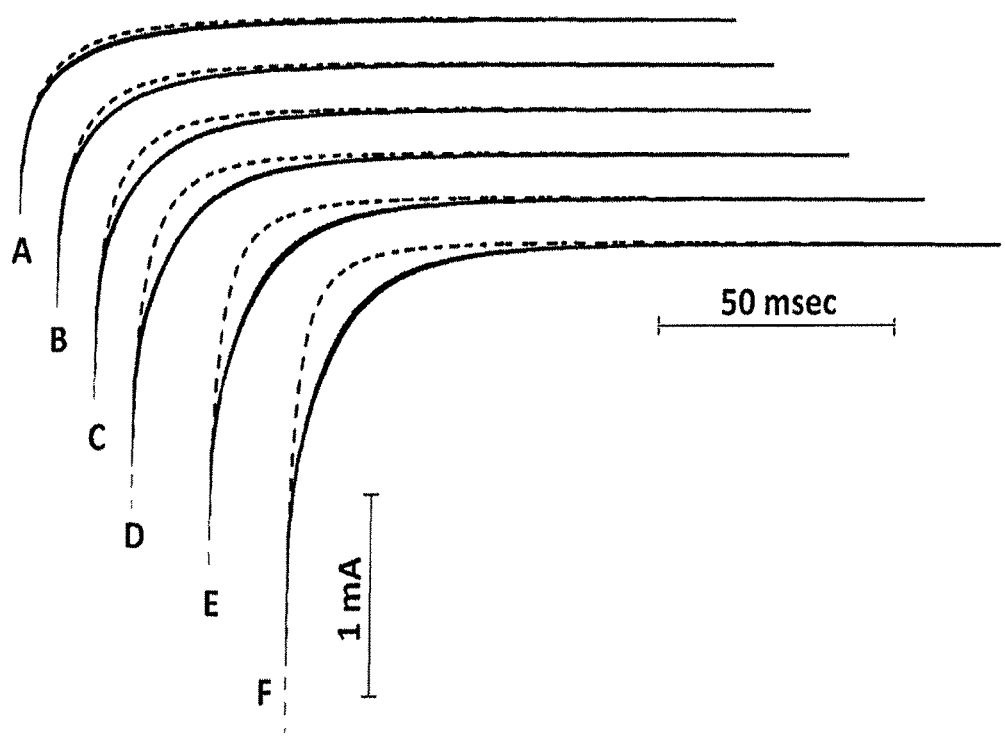
FIG. 5 shows DPS-ASC results in the form of stripping signals collected for dissolved arsenite at various concentrations, when subjected to a sequence of pulses in accordance with FIGS. 4A-4B.

Table I was prepared in view of FIG. 5, which plots the amperograms for arsenite at these concentrations: (a) 0 ppb is associated with "A", (b) 100 ppb is associated with "B", (c) 250 ppb is associated with "C", (d) 500 ppb is associated with "D", (e) 750 ppb is associated with "E", and (f) 1 ppm (associated with "F"), in 10 mM $HNO_3$/10 mM NaCl (pH 2.0). The broken line in FIG. 5 is for the first stripping pulse in connection with FIG. 4, and the solid line in FIG. 5 is for the second stripping pulse. As FIG. 5 shows, the collected stripping signals at the various concentrations have significant overlay, though not a complete overlay, of signals recorded during the first stripping pulse and the second stripping pulse, respectively. The numerical results summarized in Table 1 represent the area of these crescent-shaped areas in FIG. 5, where there is a linear relationship to the known arsenite concentrations. Further, when the adjusted charge values of Table I are plotted, they provide the same linear relationship for arsenite concentrations ranging from 100-1000 ppb, with less than 10% error over this concentration range, which again is useful in performing the background subtraction to determine charge.

What is helpful about the system and methods disclosed here is that the differences between the signal of the first stripping pulse and that of the second stripping pulse are quantifiable, and the magnitude of the differences is visually represented by the crescent-shaped areas in FIG. 5. In turn, the background-corrected stripping signal will be equivalent to the difference between the two amperograms. This value (in coulombs) is then used for Q according to the equation mentioned above, $C=Q/nFV$. Accordingly, the concentration of a metal or metal-containing species can be determined if the volume of the cell is fixed and known.

Figure 7:
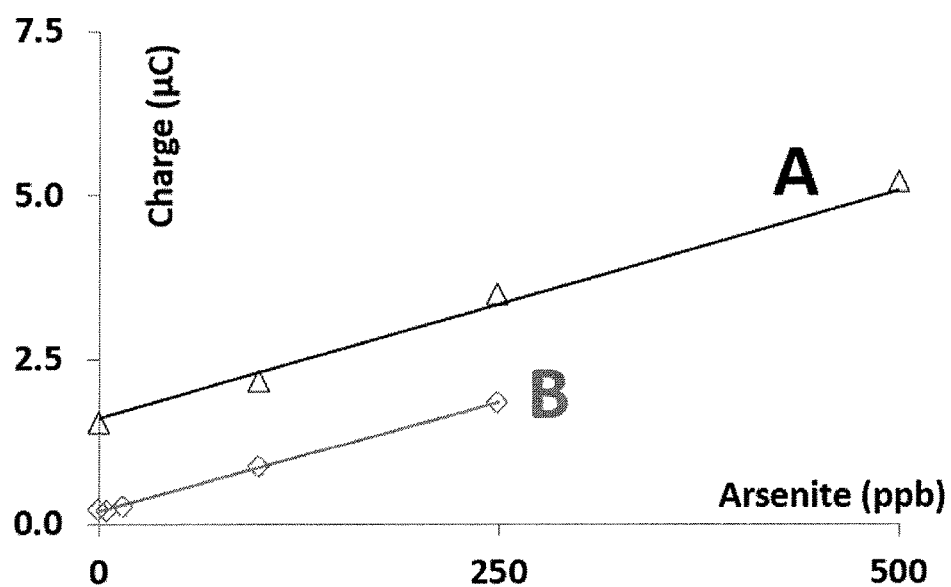
FIG. 7 is a calibration plot based on signal differences between a first stripping pulse and a second stripping pulse for arsenite at various concentrations.

Table I shows the results of DPS-ASC performed with a macro electrode. Additionally, DPS-ASC was performed with a microelectrode array (MEA), such as previously described herein with a silicon nitride layer deposited over the gold layer, then photolithographically patterned to form the MEA, as known in the art. FIG. 7 shows a comparison of the results for the macro electrode and the MEA, in that the experimentally measured charge in the platform (see, FIGS. 1 and 2, in view of the method of FIG. 4) was plotted for various concentrations based on the respective working electrodes used. A benefit of the MEA is it provides the same linear relationship for the known arsenite concentrations. Besides enhancing the signal to noise ratio, the intercept of the y-axis is reduced. The reason that the intercept for the y-axis (measured charge at 0 ppb concentration) is reduced for line "B" compared to line "A" is that the DPS-ASC method produces a signal even in blank (metal free) electrolyte solutions. This signal depends greatly on the electrode area, as well as the relative length of the first and second deposition pulses of DPS-ASC. Hence, the figure shows that reduced electrode area facilitates use of measured DPS-ASC signals directly, without further adjustment as may be needed on a macro electrode surface. Accordingly,

TABLE I

| Arsenite (ppb) | $1^{st}$ stripping pulse - Charge (μC) (RSD) | $2^{nd}$ shipping pulse - Charge (μC) (RSD) | BgC Charge (μC) ($2^{nd}$ minus $1^{st}$ stripping pulse) (RSD) | Adjusted* Charge (μC) | Calculated Charge (μC) | % Error |
|---|---|---|---|---|---|---|
| 0 | 8.73 (3.5%) | 10.27 (2.7%) | 1.54 (2.4%) | 0.00 | 0.00 | — |
| 100 | 9.20 (0.4%) | 11.38 (0.5%) | 2.19 (1.6%) | 0.65 | 0.71 | −9.0 |
| 250 | 9.60 (0.3%) | 13.10 (0.4%) | 3.50 (1.2%) | 1.96 | 1.79 | 9.5 |
| 500 | 10.08 (0.2%) | 15.28 (0.7%) | 5.21 (1.7%) | 3.67 | 3.57 | 2.6 |
| 750 | 10.00 (1.4%) | 16.81 (1.5%) | 6.81 (1.8%) | 5.27 | 5.36 | −1.8 |
| 1000 | 9.81 (1.8%) | 18.26 (2.0%) | 8.45 (2.2%) | 6.91 | 7.15 | −3.3 | the lower magnitude of the intercept allows use of Faraday's law to more accurately compute lower concentrations of arsenite from measured DPS-ASC signals, without further adjustments to account for the intercept.

The potentials used for the above examples of DPS-ASC are, of course, non-limiting. A suitable deposition potential is one that is capable of reducing all the analyte in solution and exhaustively depositing the reduced analyte on the electrode before the second stripping pulse. In some embodiments, such reduction and exhaustive deposition occurs in 60 seconds or less. However, the embodiments are not limited to cases where the stripping potential is the inverse of the deposition potential. A suitable stripping potential is one that completely strips the analyte from the electrode, generating an oxidation current having a detectable peak of a magnitude that is dependent on the metals plated during the deposition step.

Having discussed background correction involving the electrolyte, attention is now turned to correction for other dissolved metals in a sample. In stripping analysis, other metals can interfere, as they tend to co-accumulate through deposition on the electrode surface along with the specific analyte of interest. As with arsenite, the metal cations, $Cu^{2+}$, $Cd^{2+}$, and $Pb^{2+}$, completely deposit on the electrode at the −500 mV deposition potential. However, arsenite does not deposit at −300 mV, while $Cu^{2+}$, $Cd^{2+}$, and $Pb^{2+}$ do. The effect of metal interferents can most directly be corrected by variation of the deposition potential, because the deposition potential varies, but a stripping pulse of 500 mV will strip all metals from the electrode. In operation, the potentiostat targets specific potentials at which at least one metal deposits on the electrode, but at least one metal in the sample solution will not. Generally, this choice will be determined by a user for the particular analysis that is being performed, as well as the nature of the analyte(s) and possible interferents in the sample. For example, one might select −300 mV for the deposition potential because at least one metal (i.e., arsenite) does not deposit while one or more other metals in the sample solution do deposit (i.e.,).

Figure 6:
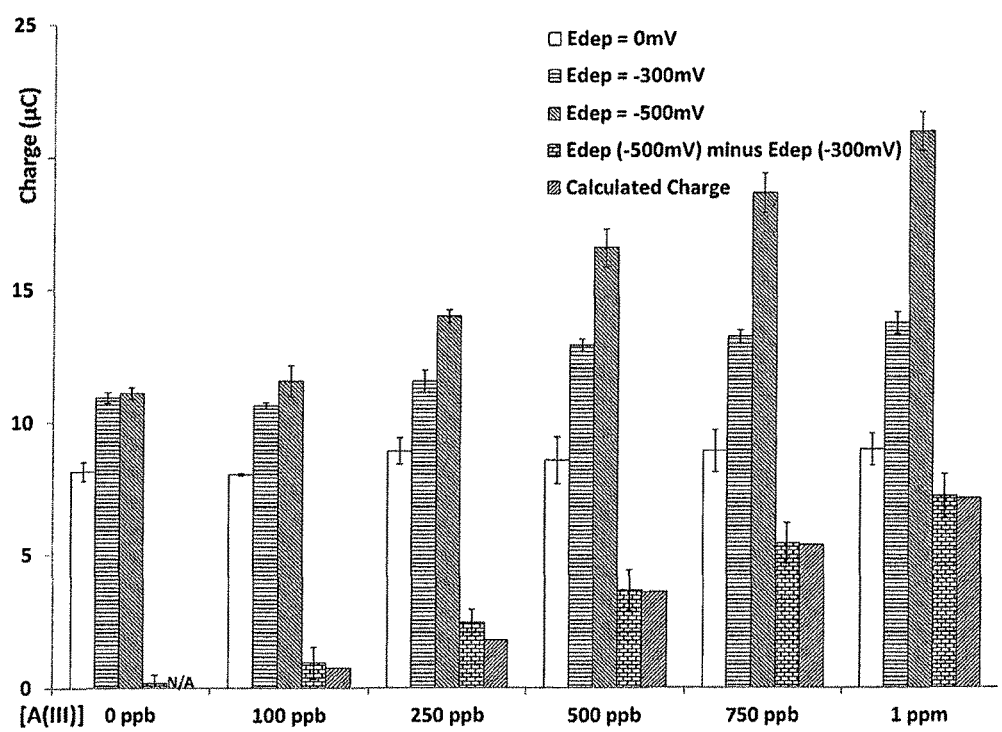
FIG. 6 shows DPS-ASC results graphically when several deposition potentials were investigated, and provides the measured charges for various concentrations of arsenite in samples, where the samples contained other metal ions and were subjected to a sequence of pulses in accordance with FIGS. 4A-4B.

In this way, differentiation between the arsenite content and the content of these potential interferents is most readily obtained by comparing the DPS-ASC signal when the deposition is carried out at −300 mV (where the stripping signal reflects the sum of $Cu^{2+}$, $Cd^{2+}$, and $Pb^{2+}$ but not arsenite) to −500 mV (where the signal reflects these $Cu^{2+}$, $Cd^{2+}$, and $Pb^{2+}$ in addition to arsenite). FIG. 6 was produced after DPS-ASC was conducted on samples containing variable arsenite concentrations, as well as 1300 ppb $Cu^{2+}$, 500 ppb $Cd^{2+}$, and 500 ppb $Pb^{2+}$. The crescent shaped areas on the amperograms were integrated to obtain the charge in microcoulombs based on Faraday's law, as described above in regards to FIG. 5. As FIG. 6 shows, for the depositions at 0 mV, only $Cu^{2+}$ is deposited at this potential; thus, the stripping charge was constant at all the arsenite concentrations. Likewise, for depositions at −300 mV, the stripping charge increased, although not always by the same amount since multiple interferents ($Cu^{2+}$, $Cd^{2+}$, and $Pb^{2+}$) are deposited at this potential. Lastly, for depositions at −500 mV, the stripping charge increased again due to the deposition of arsenite in addition to the $Cu^{2+}$, $Cd^{2+}$, and $Pb^{2+}$ interferents. At this point, direct subtraction of the −300 mV signal from the −500 mV signal yields the values that represent the background-corrected charge associated with the arsenite content of the sample. This differentiation, of the charge attributable to arsenite only, provides a practical approach to background correction. Further, this subtraction provides a partial correction of the non-zero intercept associated with the −500 mV signal, since the −300 mV signal includes a non-zero intercept where, in practice, both non-zero intercepts are of a similar magnitude. Therefore, the calculated charge based only on this difference is factored into Faraday's law, without further adjustment. With all other values of the equation being known or constant, one is able to determine the arsenite concentration in spite of the presence of other dissolved metal ions in the solution.

It will be understood that the embodiments described herein are not limited in their application to the details of the teachings and descriptions set forth, or as illustrated in the accompanying figures. Rather, it will be understood that the present embodiments and alternatives, as described and claimed herein, are capable of being practiced or carried out in various ways. Also, it is to be understood that words and phrases used herein are for the purpose of description and should not be regarded as limiting. The use herein of such words and phrases as "including," "such as," "comprising," "e.g.," "containing," or "having" and variations of those words is meant to encompass the items listed thereafter, and equivalents of those, as well as additional items.

Accordingly, the foregoing descriptions of several embodiments and alternatives are meant to illustrate, rather than to serve as limits on the scope of what has been disclosed herein. The descriptions herein are not intended to be exhaustive, nor are they meant to limit the understanding of the embodiments to the precise forms disclosed. It will be understood by those having ordinary skill in the art that modifications and variations of these embodiments are reasonably possible in light of the above teachings and descriptions.

What is claimed is:

1. A method of analyzing dissolved metals in a sample solution, the sample solution being contained in a cell having a fixed and known volume, the method comprising:

initiating a first reduction reaction in the sample solution which contains two or more dissolved metals by applying a first deposition potential for an interval of time representing a first deposition pulse, wherein the first reduction reaction results in non-exhaustive deposition of one or more of the dissolved metals upon an electrode, wherein the one or more dissolved metals deposited during the first reduction reaction comprise one or more interferents;

initiating a first oxidation reaction by applying a stripping potential for an interval of time, representing a first stripping pulse, that is sufficient to strip the one or more interferents from the electrode that were deposited during the first reduction reaction, and measuring electrical current generated during the first stripping pulse;

after the first oxidation reaction, initiating a second reduction reaction by applying a deposition potential for an interval of time, representing a second deposition pulse, that results in exhaustive deposition of the one or more interferents upon the electrode;

initiating a second oxidation reaction by applying a stripping potential for an interval of time, representing a second stripping pulse, that is sufficient to strip all the one or more interferents from the electrode that were deposited during the second reduction reaction, and measuring electrical current generated during the second stripping pulse;

after the second oxidation reaction, initiating a third reduction reaction in the sample solution by applying a second deposition potential different from the first deposition potential for an interval of time representing a third deposition pulse, wherein the third reduction reaction results in non-exhaustive deposition of the one or more dissolved metals comprising the one or more interferents and at least one analyte upon the electrode;

initiating a third oxidation reaction by applying a stripping potential for an interval of time, representing a third stripping pulse, that is sufficient to strip the one or more interferents and the at least one analyte from the electrode that were deposited during the third reduction reaction, and measuring electrical current generated during the third stripping pulse;

after the third oxidation reaction, initiating a fourth reduction reaction by applying a deposition potential different from the first deposition potential, for an interval of time that results in exhaustive deposition of the one or more interferents and the at least one analyte upon the electrode;

initiating a fourth oxidation reaction by applying a stripping potential for an interval of time, representing a fourth stripping pulse, that is sufficient to strip the one or more interferents and the at least one analyte from the electrode that were deposited during the fourth reduction reaction, and measuring electrical current generated during the fourth stripping pulse; and calculating a concentration of the at least one analyte in the sample solution based on a quantitative difference between the absolute charge associated with stripping the one or more interferents from the electrode, subtracted from the absolute charge associated with stripping the one or more interferents and the at least one analyte from the electrode.

2. The method of claim 1, wherein the absolute charge associated with stripping the one or more interferents from the electrode is the difference between the electrical current generated during the first stripping pulse, subtracted from the electrical current generated during the second stripping pulse, and wherein the absolute charge associated with stripping the one or more interferents and the at least one analyte from the electrode is the difference between the electrical current generated during the third stripping pulse, subtracted from the electrical current generated during the fourth stripping pulse.

3. The method of claim 1, wherein the first deposition pulse results in more than zero and less than about 5% of the one or more interferents in the sample solution being deposited on the electrode.

4. The method of claim 1, wherein the third deposition pulse results in more than zero and less than about 5% of the one or more interferents and the at least one analyte in the sample solution being deposited on the electrode.

5. A method of analyzing dissolved metals in a sample solution, the sample solution being contained in a cell having a fixed and known volume, the method comprising:

initiating a first reduction reaction in the sample solution which contains two or more dissolved metals, by applying a first deposition potential for an interval of time representing a first deposition pulse, wherein the first reduction reaction results in non-exhaustive deposition of one or more of the dissolved metals upon an electrode, wherein the one or more dissolved metals deposited during the first reduction reaction comprise one or more interferents and at least one analyte;

initiating a first oxidation reaction by applying a stripping potential for an interval of time, representing a first stripping pulse, that is sufficient to strip the one or more interferents and the at least one analyte from the electrode that were deposited during the first reduction reaction, and measuring electrical current generated during the first stripping pulse;

after the first oxidation reaction, initiating a second reduction reaction by applying a deposition potential for an interval of time, representing a second deposition pulse, that results in exhaustive deposition of the one or more interferents and the at least one analyte upon the electrode;

initiating a second oxidation reaction by applying a stripping potential for an interval of time, representing a second stripping pulse, that is sufficient to strip all the one or more interferents and the at least one analyte from the electrode that were deposited during the second reduction reaction, and measuring electrical current generated during the second stripping pulse;

after the second oxidation reaction, initiating a third reduction reaction in the sample solution by applying a second deposition potential different from the first deposition potential for an interval of time representing a third deposition pulse, wherein the third reduction reaction results in non-exhaustive deposition of the one or more interferents but not of the at least one analyte;

initiating a third oxidation reaction by applying a stripping potential for an interval of time, representing a third stripping pulse, that is sufficient to strip the one or more interferents from the electrode that were deposited during the third reduction reaction, and measuring electrical current generated during the third stripping pulse;

after the third oxidation reaction, initiating a fourth reduction reaction by applying a deposition potential different from the first deposition potential, for an interval of time that results in exhaustive deposition of the one or more interferents upon the electrode;

initiating a fourth oxidation reaction by applying a stripping potential for an interval of time, representing a fourth stripping pulse, that is sufficient to strip the one or more interferents from the electrode that were deposited during the fourth reduction reaction, and measuring electrical current generated during the fourth stripping pulse; and calculating a concentration of the at least one analyte in the sample solution based on a quantitative difference between the absolute charge associated with stripping the one or more interferents from the electrode, subtracted from the absolute charge associated with stripping the one or more interferents and the at least one analyte from the electrode.

6. The method of claim 5, wherein the absolute charge associated with stripping the one or more interferents and the at least one analyte from the electrode is the difference between the electrical current generated during the first stripping pulse, subtracted from the electrical current generated during the second stripping pulse, and wherein the absolute charge associated with stripping the one or more interferents from the electrode is the difference between the electrical current generated during the third stripping pulse, subtracted from the electrical current generated during the fourth stripping pulse.

7. The method of claim 5, wherein the first deposition pulse results in more than zero and less than about 5% of the one or more interferents and the at least one analyte in the sample solution being deposited on the electrode.

8. The method of claim 5, wherein the third deposition pulse results in more than zero and less than about 5% of the one or more interferents in the sample solution being deposited on the electrode.

* * * * *